(12) United States Patent
Perez et al.

(10) Patent No.: US 9,475,045 B2
(45) Date of Patent: Oct. 25, 2016

(54) MICROPOROUS ORGANOGEL ABSORBING/SOLUBILISING MATERIALS

(71) Applicant: CENTRE NATIONAL DE LA RECHERCHE SCIENTIFIQUE (CNRS), Paris (FR)

(72) Inventors: Emile Perez, Colomiers (FR); Sophie Franceschi-Messant, Pechbusque (FR); Isabelle Rico-Lattes, Auzielle (FR); Jean-Christophe Garrigues, Toulouse (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 543 days.

(21) Appl. No.: 13/839,942

(22) Filed: Mar. 15, 2013

(65) Prior Publication Data
US 2014/0013867 A1    Jan. 16, 2014

Related U.S. Application Data

(60) Provisional application No. 61/667,642, filed on Jul. 3, 2012.

(30) Foreign Application Priority Data

Mar. 30, 2012 (FR) ...................... 12 52902

(51) Int. Cl.

| | | |
|---|---|---|
| *B01J 20/291* | (2006.01) | |
| *B01J 20/285* | (2006.01) | |
| *C02F 101/30* | (2006.01) | |
| *C09K 3/32* | (2006.01) | |
| *B01L 3/00* | (2006.01) | |
| *B01D 53/02* | (2006.01) | |
| *C02F 1/28* | (2006.01) | |
| *G01N 1/22* | (2006.01) | |
| *B01D 15/08* | (2006.01) | |
| *G01N 1/10* | (2006.01) | |
| *G01N 30/06* | (2006.01) | |
| *B01J 20/26* | (2006.01) | |
| *B01J 20/30* | (2006.01) | |
| *B01J 20/28* | (2006.01) | |
| *C02F 101/32* | (2006.01) | |
| *C02F 103/00* | (2006.01) | |
| *C02F 1/40* | (2006.01) | |

(52) U.S. Cl.
CPC ............. *B01L 3/5023* (2013.01); *B01D 15/08* (2013.01); *B01D 53/02* (2013.01); *B01D 53/025* (2013.01); *B01J 20/268* (2013.01); *B01J 20/285* (2013.01); *B01J 20/28047* (2013.01); *B01J 20/291* (2013.01); *B01J 20/3064* (2013.01); *B01L 3/502707* (2013.01); *C02F 1/285* (2013.01); *C09K 3/32* (2013.01); *G01N 1/10* (2013.01); *G01N 1/2214* (2013.01); *G01N 30/06* (2013.01); *B01D 2253/20* (2013.01); *B01D 2253/202* (2013.01); *B01D 2253/308* (2013.01); *B01D 2253/311* (2013.01); *B01D 2257/708* (2013.01); *B01D 2257/93* (2013.01); *B01J 2220/82* (2013.01); *C02F 1/40* (2013.01); *C02F 2101/32* (2013.01); *C02F 2103/007* (2013.01); *C02F 2305/14* (2013.01)

(58) Field of Classification Search
CPC . B01L 3/502746; F28F 13/06; B01J 20/285; B01J 20/291
See application file for complete search history.

(56) References Cited

FOREIGN PATENT DOCUMENTS

| | | |
|---|---|---|
| CN | 102139203 A | 8/2011 |
| EP | 1566213 A1 | 8/2005 |
| FR | 2886867 A1 | 12/2006 |
| JP | 2012046596 A | 3/2012 |
| WO | 2006/134299 A1 | 12/2006 |

OTHER PUBLICATIONS

Venditti et al., "Removal of chromate from water by a new CTAB-silica gelatin composite." Journal of Colloidal and Interface Science; 310 (2007) 353-361.
Venditti et al., "Effects of sulfate ions and slightly acidic pH conditions on Cr(VI) adsorption onto silica gelatin composite." Journal of Hazardous Materials; 173 (2010) 552-557.
Maity et al., Fabrication of nanoporous materials from a hydrophobic peptide. CrystEngComm; 13 (2011) 3064-3071.
Lukyanova et al., "Colloids and Surfaces B: Biointerfaces." Elsevier B.V.; 79 (2010) 105-112.
Thesis Presented by Lukyanova, Jan. 22, 2009: "Preparation de Matrices Microporeuses D'organogels et Evaluation en Culture Cellulaire." Universite de Toulouse.
Lukyanova et al., "Soft Microporous Green Materials from Natural Soybean Oil." ChemSusChem 1 (2008) 514-518.
Press Article: "Ces substances qui polluent la Garonne;" (May 29, 2011) and English translation thereof.

*Primary Examiner* — Paul Hyun
(74) *Attorney, Agent, or Firm* — Birch, Stewart, Kolasch & Birch, LLP

(57) ABSTRACT

The present invention concerns the use of a microporous organogel for trapping fluids by adsorption and/or for the controlled release of fluids after solubilization. The fluids are particularly air or water polluting agents or volatile substances. The invention also concerns the use of a microporous organogel in a method for analyzing the trapped fluids. The invention also concerns any fluid trap obtained by molding a microporous organogel.

19 Claims, 3 Drawing Sheets

MICROPOROUS ORGANOGEL ABSORBING/SOLUBILISING MATERIALS

CROSS REFERENCE TO RELATED APPLICATIONS

This application claims priority to FR 1252902 filed Mar. 30, 2012 and U.S. Ser. No. 61/667,642 filed Jul. 3, 2012, each of which is incorporated herein by reference in their entireties.

BACKGROUND

1. Field of the Invention

The present invention concerns the use of novel microporous organogels as adsorbents and solubilising agents in the area concerning the trapping of fluids.

2. Description of Related Art

Before they can be analysed, fluids which by definition group together gases or liquids must be trapped. The fields of application are varied and diverse, and mention may be made for example of the analysis of polluting agents or fragrances whether or not in the form of volatile compounds.

Nevertheless, the adsorbent materials used at the present time are very rapidly saturated on the surface which prevents the trapping of fluids in large amounts.

In addition, the porous adsorbents currently available are of mineral origin (activated charcoal, zeolite, clays) or synthetic polymers.

The trapped products are difficult to recover and the density, porosity and polarity of these materials cannot be adjusted.

These materials are also difficult to regenerate leading to high costs of use.

Additionally, there is a true need at the current time to develop new materials in the field of fluid trapping.

SUMMARY

In surprising manner, the Applicant has evidenced the use of microporous organogels in the area of fluid adsorption, which can be efficiently applied to the trapping of fluids since they are capable of solubilising the adsorbed fluids.

DETAILED DESCRIPTION OF A PREFERRED EMBODIMENT

Figure 1:
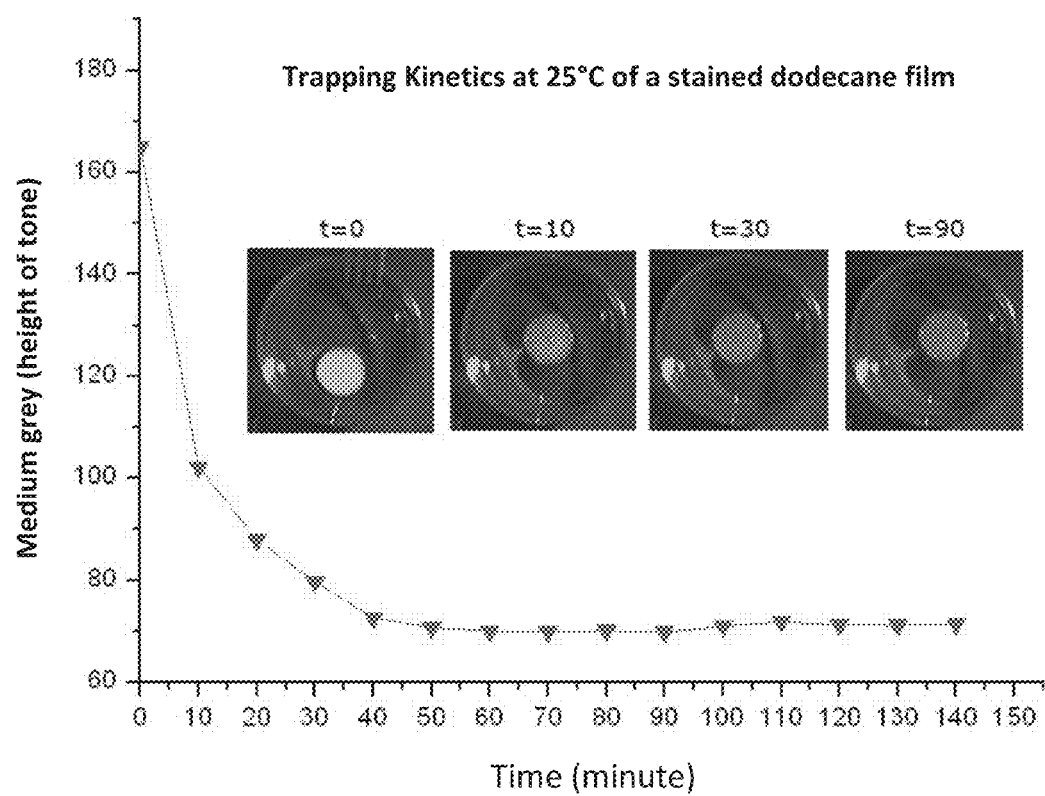
FIG. 1 shows a curve of the trapping kinetics at 25° C. of a stained dodecane film.

Organogels are semi-solid materials consisting of an organic liquid or oil immobilized by a three-dimensional network of fibres resulting from the self-assembly of a polymer organogelator or low molecular weight organogelator.

A low molecular weight organogelator corresponds to a small organic molecule capable of gelling in small proportions a broad range of organic liquids. By low molecular weight is meant a molecular weight of less than 1000 g/mol, and more particularly less than 500 g/mol.

It is to be noted that the content of organogelator controls the heat resistance of the organogel but also its mechanical strength. This parameter therefore allows easy adapting of the material in relation to use-related constraints.

Also, the polarity of the organogel depends on the organic liquid or oil to be gelled. On this account, the use of a vegetable oil of strong hydrophobic nature will allow a hydrophobic organogel to be obtained.

Microporous organogels are used in cosmetics, pharmaceuticals or foodstuffs and have the advantage of being able to contain ingredients or active ingredients to facilitate the stability and the adding of the said ingredients or active ingredients to compositions.

More particularly, microporous organogels can be used in tissue engineering to prepare artificial extracellular matrices as described in the thesis by Lukyanova, 22 Jan. 2009: "Preparation de matrices microporeuses d'organogels et evaluation en culture cellulaire" and in the article by Lukyanova et al.: "Colloids and Surfaces B"; Biointerfaces, 2010, 79, 105-112.

These microporous organogels are obtained via the method described in the thesis by Lukyanova and in the article by Lukyanova et al.: "Soft Microporous Green Materials from Natural Soybean Oil"; ChemSusChem, 2008, 1, 514-518.

For the preparation of these organogels, one particularly suited organogelator is 12-hydroxystearic acid (HSA) derived from castor oil. More particularly, 12-hydroxystearic acid is able to form organogels with organic aliphatic, alicyclic or aromatic liquids. It is also able to form organogels with vegetable oils such as sunflower oil and soybean oil.

A method using the aqueous dissolution of a template of solid water-soluble particles of calibrated size allows controlled microporosity to be obtained inside the organogels. These water-soluble solid particles are more commonly called porogens.

To obtain a microporous organogel, a first step consists of preparing templates of water-soluble porogens, in particular sugars such as sucrose for example or icing sugar, or salts such as sodium chloride for example, by agglomeration with a minimum amount of water. The paste obtained is then pressed in a mould and dried to obtain compact templates of porogens.

At a second step, these compact templates of porogens are immersed in the molten organogel in liquid form.

After impregnation, the mixture is cooled and the templates impregnated with organogel are immersed in distilled water at ambient temperature until complete dissolution of the porogens particles, thereby forming pores inside the organogel.

Table 1 below groups together data corresponding to pore size distribution and effective porosity in relation to the type of porogen, type of oil and to the initial water content of the template.

TABLE 1

Composition and characteristics of matrices containing capric/caprylic triglycerides and soybean oil

| Organogel | Porogen agent | Initial water content, wt. % | Pore size distribution (mean) [a], μm | Effective porosity [b], % |
|---|---|---|---|---|
| Capric/ caprylic triglycerides (15 wt. % | Sugar | 3.5 | 25-400 (220) | 65.2 ± 1.5 |
| | | 2 | 25-500 (290) | 64.3 ± 0.4 |
| | Salt (NaCl) | 3.5 | 25-500 (230) | 61.9 ± 1.6 |
| | | 2 | 25-500 (230) | 59.9 ± 1.3 |

TABLE 1-continued

Composition and characteristics of matrices
containing capric/caprylic triglycerides and soybean oil

| Organogel | Porogen agent | Initial water content, wt. % | Pore size distribution (mean) [a], μm | Effective porosity [b], % |
|---|---|---|---|---|
| HSA) [c] | Salt | 3.5 | 25-300 (150) | 60.2 ± 1.0 |
| | (NaCl) | 2 | 25-350 (150) | 61.7 ± 1.5 |
| | Icing | 3.5 | 10-75 (30) | 66.3 ± 1.7 |
| | sugar | 2 | 10-60 (40) | 59.7 ± 1.1 |
| Soybean oil | Sugar | 3.5 | 25-400 (220) | 64.5 ± 1.2 |
| (7.5 wt. % | | 2 | 25-500 (270) | 60.9 ± 0.8 |
| HSA) [c] | Salt | 3.5 | 25-500 (230) | 61.1 ± 1.9 |
| | (NaCl) | 2 | 25-550 (230) | 55.7 ± 2.1 |
| | Icing | 3.5 | 10-70 (30) | 64.1 ± 0.9 |
| | sugar [d] | 2 | 10-60 (40) | 57.9 ± 1.3 |

[a] Determined by image analysis;
[b] measured by liquid displacement;
[c] matrices with 30% HSA for the capric/caprylic triglycerides and 15% HSA for soybean oil give identical results;
[d] soybean oil organogel containing icing sugar with 15 wt. % HSA.

These novel microporous organogels, such as characterized in Table 1 and defined in the prior art, have shown good biodegradability. In addition, the mechanical strength of these porous matrices is fully adapted for the reconstruction of soft tissue. In vitro biological tests on these microporous organogels have allowed the evaluation of their capacity as artificial extracellular matrix for the culture of fibroblasts. It has also been evidenced that these matrices prove to be capable of maintaining the survival and proliferation of cells over a long period of 21 days. To conclude, the potential of these novel microporous organogels as artificial extracellular matrices has been evidenced for tissue engineering.

The subject of the present invention is therefore the use of a microporous organogel for trapping fluids by adsorption and/or for the controlled release of fluids after solubilisation.

Advantageously, the fluids are concentrated in the microporous organogel.

According to one particular aspect of the invention, the fluids contain organic compounds.

By concentration of a fluid in the microporous organogel is meant an increase in the quantity of fluid matter within the microporous organogel leading to a reduction in the equivalent quantity of fluid matter in the outside medium (water or air). Concentration is therefore taken in the meaning of the partition ratio of a fluid between water or air and the microporous organogel.

Adsorption is based on the property of solid or gelled surfaces to fix molecules of gas or liquids reversibly via weak bonds of Van der Walls type.

The fluids adsorbed on the surface are solubilised in the organogel on account of its gelled liquid nature.

By controlled release is meant the isolating of the adsorbed fluid after solubilisation of the microporous organogel. The mechanism of controlled release is based on the oil/water or oil/air partition ratio of the fluid but also on the fibrous network of the microporous organogel whose density and meshing limit free diffusion.

By organic compound is meant a molecule comprising at least one carbon atom.

According to one particular aspect of the invention, the fluids contain air or water polluting agents, in particular hydrocarbons and/or heavy metals.

Polluting agents in the meaning of the present invention are molecules which, beyond a certain threshold, develop negative impacts on an ecosystem or an environment in general. Typically, the polluting agents may be hydrocarbons i.e. organic compounds exclusively containing atoms of carbon and hydrogen. The polluting agents may also be heavy metals qualified as such on account of their high density. Mention may be made for example of lead, cadmium, mercury, arsenic, chromium, nickel, copper, zinc.

Therefore in one particularly advantageous field of application of the invention, the microporous organogel is used to trap polluting agents.

Indeed, numerous human and industrial activities are the source of organic and hydrophobic pollutants such as pesticides, herbicides, or hydrocarbons and motor vehicle oils (lubricants, brake fluid, hydraulic fluids). Some surface pollution is very visible in particular that caused by detergents which foam on the surface of water, or oil spills which are veritable ecological catastrophes.

However, there exists a surface pollution that is underestimated, whose composition is ill-identified and is hence much more insidious.

These last types of pollutants are often less dense than water and therefore form surface pollution. Hydrophobic pollutants may also exist in emulsified form obtained after shearing by wind or rain. This emulsified form is metastable and after creaming will produce a surface film.

Indeed, hydrophobic surface films may prove to be highly polluting. The thin interface layer lying between water and air, called neuston, forms the communication gateway between these two environments and its deterioration may have serious consequences on exchanges between the two. This interface may accumulate hydrophobic pollutants on the surface, these pollutants having a greater or lesser physical and chemical barrier effect.

Neuston corresponds to the surface of oceanic and inland waters and covers more than 70% of the world surface area, its biodiversity including several thousand species. Pollution which accumulates thereupon may therefore have serious consequences for its inhabitant organisms. In addition the mix of all these pollutants, spread out and concentrated in a thin layer, is exposed to intense radiation which may lead to other even more harmful pollutants.

In addition, surface pollutants are mostly non-volatile residues of hydrocarbons (petrol, diesel oil) or motor vehicle oils (engine lubricants, brake fluid, hydraulic fluids). The accumulation of these pollutants in rainwaters from road networks, airports or port installations raises concerns as to the possible repercussions on public health and the biodiversity of aquatic environments.

Also, the characterization and quantification of these hydrophobic surface pollutants is not easy. These pollutants remain very difficult to capture. This difficulty is related to the fact that these pollutants extend over very large surface areas, often in very thin films, and conventional water sampling methods only allow an infinitely small proportion thereof to be harvested which often does not lend itself to detection. Therefore although the presence of these surface pollutants has been proven, their extent and composition are not precisely known nor are all the impacts they may have on the environment.

Within this context, the microporous organogel used in the present invention is particularly suited on account of its low density, which in particular is lower than that of water thereby leading to its buoyancy. The microporous organogel is therefore able to absorb and solubilise in large quantity various types of hydrophobic pollutants present in water, whether emulsified or in thin surface films.

According to another aspect of the invention, the fluids are volatile substances, particularly gases or vapours, and preferably pheromones of insects, aromas of plants, flowers or resins.

The property of fats and oils of adsorbing scents has been ascertained since antiquity. This method allowed the use of plant aromas for hundreds of years. This method known as extraction with animal fats was reserved for fragile flowers and is described in particular in the article by Lawrence et al.: Progress in essential oils, Perfumer & flavorist 1994, 19(5), 83. The principle is based on the greater solubility of odoriferous molecules in oil than in plant products with the natural transfer of scents from the plant to the fat or oil.

The microporous organogel of the invention is therefore particularly advantageous in that it forms a microporous fat having a very high specific surface area promoting adsorption.

Typically, the microporous organogel used in the present invention is hydrophobic. By hydrophobic is meant the fact that the gelled liquid is non-polar or scarcely polar, and that it cannot set up bonds or interactions with water.

In particular, the microporous organogel used in the present invention has a porosity of between 10% and 90%, preferably between 55 and 70%.

The percentage porosity of the microporous organogel is obtained and calculated using the following method:
 The water-saturated microporous organogel is weighed and a weight M1 is obtained.
 The microporous organogel is then dehydrated by lyophilisation and is again weighed to obtain a weight M2.
 The trapped weight of water M0 is equal to M1−M2.
 The volume occupied by the water V1 is equal to M0/d1 (d1=density of water)
 The volume occupied by the organogel is equal to M2/d2 (d2=density of the organogel)
 The percentage porosity is equal to (V1/(V1+V2))×100.

More particularly, the mean diameter of the pores of the microporous organogel used in the present invention is between 0.5 µm and 550 µm, preferably 220 µm.

The invention also concerns the use of a microporous organogel such as defined above, obtained using a method comprising a step to prepare the organogel and a step to form pores in the said organogel, in particular by aqueous dissolution of a template of solid water-soluble particles of calibrated size, previously impregnated with organogel, preferably of sugars advantageously sucrose, or of salts advantageously sodium chloride.

Advantageously the microporous organogel is prepared from an organogelator in particular 12-hydroxystearic acid and from an organic liquid non-miscible in water, in particular an oil, preferably soybean oil.

The invention also concerns the use of a microporous organogel such as defined above in a method for analysing trapped fluids, in particular by liquid or gas chromatography and/or by mass spectrometry and/or as substrate for solid phase extraction (SPE).

Advantageously, the analysis of the trapped fluids is performed by simple dissolution of the organogel used in the present invention in a suitable solvent.

As suitable solvent, mention may be made organic solvents, in particular tetrahydrofuran.

The invention also concerns any fluid trap which has been shaped to a suitable form by moulding a microporous organogel such as defined above.

By suitable shape is meant a geometric shape of the trap that is adapted to the trapping area and trapping medium of the fluids. For example, a disc or plate shape is well adapted for trapping fluids on the surface of water but much less so for trapping at depth. In this case a sphere or cylinder shape is preferred.

Therefore, the use of a microporous organogel such as defined above for trapping fluids has numerous advantages.

Indeed, its unique twofold property of adsorption and solubilisation allows the trapping and accumulating of large quantities of fluids. The technique for preparing the microporous organogel is clean and low-cost and provides for controlled porosity by adjusting pore volume and pore size. This preparation technique also allows the density and polarity of the microporous organogel to be adjusted in relation to the type of gelled liquids and their mixture and in relation to the choice of organogelator.

The ingredients used to obtain the microporous organogel are derived from renewable resources and the preparation method pays heed to the environment.

Microporous organogels also allow direct analysis of the trapped fluids by simple dissolution in a suitable solvent.

The following examples are used to illustrate but in no way limit the invention.

FIG. 1 shows a curve of the trapping kinetics at 25° C. of a stained dodecane film.

Figure 2:
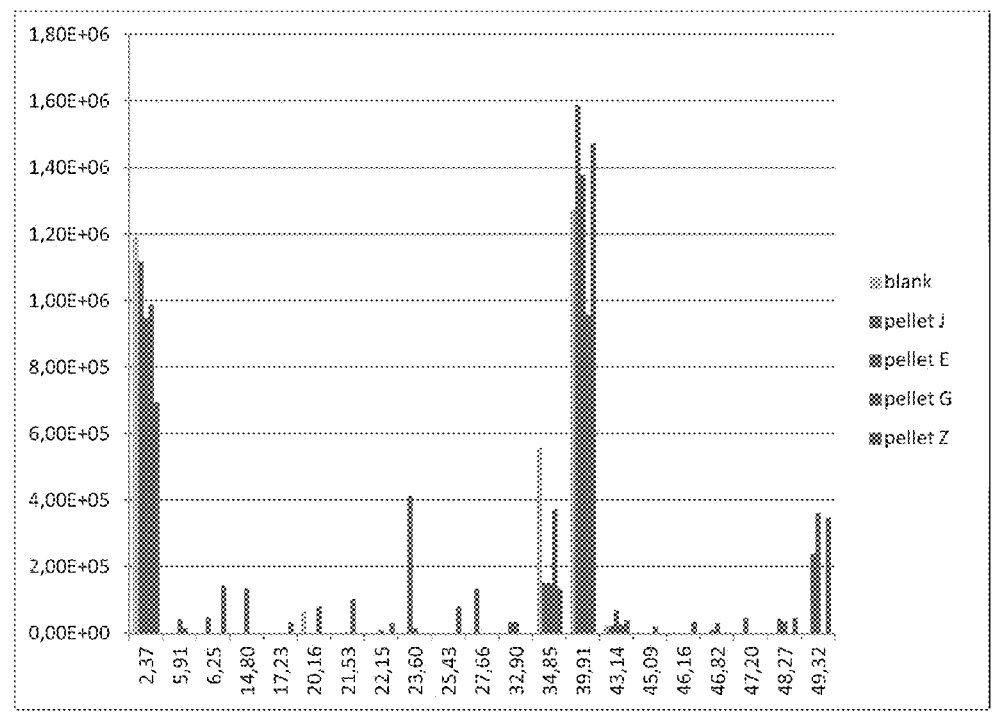
FIG. 2 is a chromatogram of lavender aromas trapped by the microporous organogel used in the invention.

FIG. 2 is a chromatogram of lavender aromas trapped by the microporous organogel used in the invention.

Figure 3:
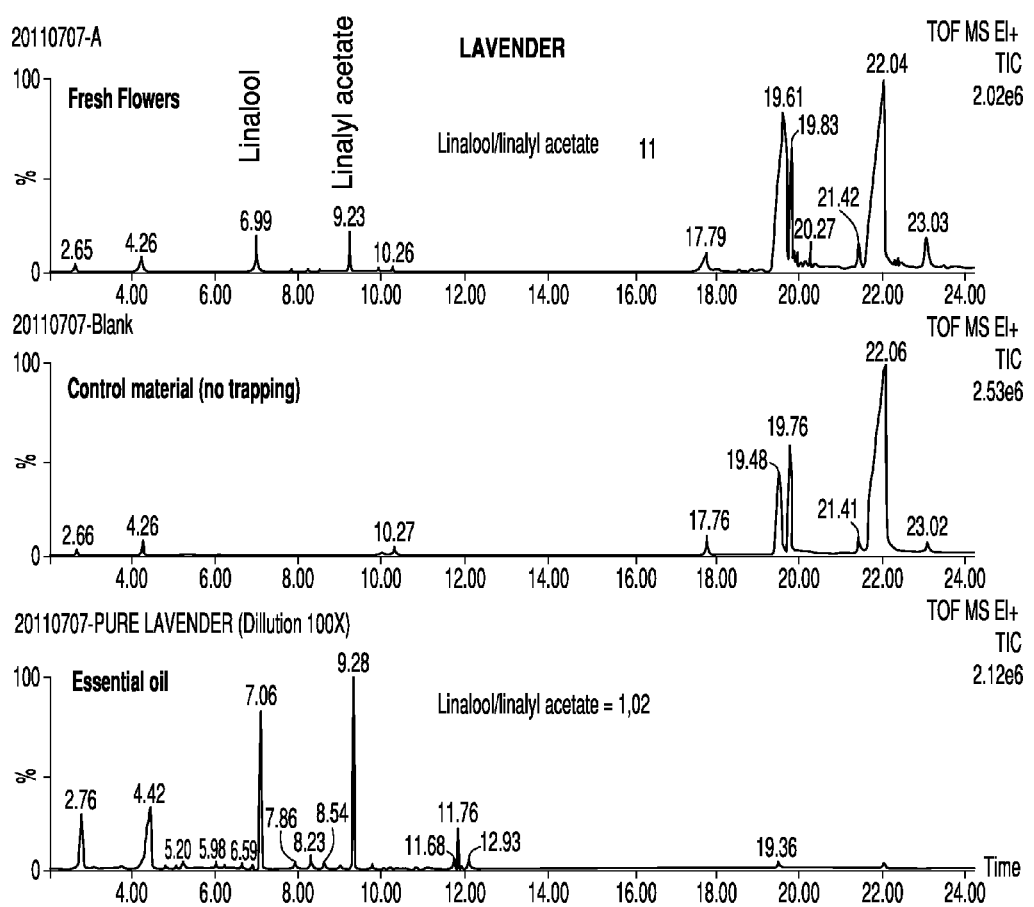
FIG. 3 is a chromatogram of fluids trapped by different pellets of microporous organogel used in the invention.

FIG. 3 is a chromatogram of fluids trapped by different pellets of microporous organogel used in the invention.

EXAMPLE A

Demonstration of the Trapping of a Hydrocarbon Film on a Water Surface

Hydrocarbon Model:
Dodecane stained with vermilion red (5% v/v)
Trap:
pellet of microporous organogel (soybean oil, HSA organogelator (15 weight %), sugar template).
Pellet characteristics: Dehydrated pellet, diameter=30 mm, thickness=5 mm, mean porosity 67%, mean pore diameter 220 µm.
Trapping Protocol and Kinetic Monitoring:
A film of stained dodecane 1 mm thick is formed on a water surface. On this film a pellet is deposited whose staining is filmed over time. Image analysis software allows monitoring of the adsorption kinetics by photodensitometry.
Results:
The kinetics curve (FIG. 1) shows rapid adsorption of the dodecane film with a plateau after 60 min.
Remark:
A non-dehydrated pellet has the same adsorption capacities with slightly slower kinetics (plateau after 75 min)

EXAMPLE B

Demonstration of the On-Site Trapping of Surface Pollutants

Test Site:
Lac du Perget in Colomiers (31770)
Trap:
pellet of microporous organogel (soybean oil, HSA organogelator (15 weight %), sugar template).
Pellet characteristics: Dehydrated pellet, diameter=30 mm, thickness=5 mm, mean porosity 67%, mean pore diameter 220 µm.

Trapping Protocol:

The pellet is deposited on the surface of the water inside a floating hoop (30 cm in diameter) to delimit a trapping surface. The pellet is recovered after 2 hours.

Controls:

Non-trapping pellet.

GC Analysis:

HPLC-UV analyses performed on an Alliance 2695 system, with PDA 996, Xbridge Shield column RP18, 2.1×100 mm, 3.5 µm. Gradient T0: 100% $H_2O$, T60 min: 100% ACN, flow rate 0.3 ml/min. UV analysis at 230 nm. Solubilisation of the pellet in:

1 ml THF, injection 10 µL.

Results:

FIG. 2 shows that in the different pellets analysed (pellets J, E, G and Z), between 2 and 8 peaks characteristic of surface pollution were identified, since they were not found in the analysis of the control pellet (blank).

EXAMPLE C

Demonstration of Scent Trapping

Plant Tested:

True lavender (*Lavandula angustifolia*), fresh flowers and essential oil.

Trap:

pellet of microporous organogel (soybean oil, HSA organogelator (15 weight %), sugar template).

Characteristics of the Pellet:

Dehydrated pellet, diameter=30 mm, thickness=5 mm, mean porosity 67%, mean pore diameter 220 µm.

Trapping Protocol:

Pellet suspended above the flowers in a hermetically sealed bowl, for 1 hour at 25° C.

Controls:

Pellet without trapping and direct injection of the essential oil.

GC Analysis:

After trapping, the pellets were dissolved in 1 ml de THF and analysed by gas phase chromatography coupled with detection by mass spectrometry.

Results:

The chromatogram shown in FIG. 3 corresponds to 3 analyses: essential oil injected directly, a control pellet and trapping on fresh flowers.

The peaks at 7.0 and 9.2 minutes respectively correspond to linalool (L) and linalyl acetate (AL), the 2 main odorant molecules of lavender. Their presence confirms the adsorbing efficacy of the material on volatile compounds. The ratios of these 2 peaks (L/AL) are equivalent in the essential oil and in the trapping on fresh flowers, which indicates that after adsorption in the material the olfactory signature is maintained.

EXAMPLE D

Preparation of the Microporous Organogel

1. Preparation of the Organogel

Fixed concentrations of gels are obtained by adding weighed quantities of 12-hydroxystearic acid to soybean oil and the mixture is heated to 70° C. (>T° gelling). The solution is cooled to ambient temperature and a gel is obtained. The gel state is confirmed using the upturned bottle test.

2. Formation of the Pores

Templates of particles of agglomerated porogens (sucrose, sodium chloride) are prepared by mixing porogen particles with 2 or 3.5 weight % of distilled water. The paste mixture is manually pressed in a Teflon® mould and dried for 30 to 35 minutes at 80° C. The templates of agglomerated porogen particles are then immersed in the molten organogel at a temperature of 70° C. (>T° gelling), and left for 12 to 15 minutes for good impregnation of the templates. After cooling to ambient temperature, the impregnated and gelled models are immersed at ambient temperature in distilled water renewed every day for 7 days to dissolve the porogen particles and then air dried.

The invention claimed is:

1. A method for trapping one or more hydrophobic pollutants in fluids containing said pollutants, comprising contacting the said fluids with a microporous organogel to thereby solubilize said fluids in said organogel;
dissolving said organogel in an organic solvent; and
isolating said fluid containing said pollutants.

2. The method according to claim 1, wherein the fluids are concentrated in the microporous organogel.

3. The method according to claim 1, wherein the fluids comprise organic compounds.

4. The method according to claim 1, wherein the fluids comprise air and/or water polluting agents.

5. The method according to claim 1, wherein the fluids comprise volatile substances.

6. The method according to claim 1 wherein the microporous organogel is hydrophobic.

7. The method according to claim 1 wherein the microporous organogel has a porosity of from 10 to 90%.

8. The method according to claim 1 wherein the mean diameter of the pores of the microporous organogel is from 0.5 µm to 550 µm.

9. A method for analysing one or more trapped fluids which comprises trapping one or more hydrophobic pollutants with the method of claim 1, subsequent to the dissolution of the organogel and isolation of the fluids, analyzing said fluids by liquid or gas chromatography, or by mass spectrometry or as substrate for solid phase extraction (SPE).

10. The method according to claim 1, wherein the microporous organogel has a porosity of from 55 to 70%.

11. The method according to claim 1 wherein the mean diameter of the pores of the microporous organogel is 220 µm.

12. The method according to claim 1, wherein the fluids comprise hydrocarbons or heavy metals.

13. The method according to claim 1, wherein the fluids comprise gases or vapours.

14. The method according to claim 1, wherein the fluids contain insect pheromones, aromas of plants, flowers, or resins.

15. The method according to claim 1 wherein the microporous organogel is obtained using a method comprising preparing the organogel and forming pores in said organogel by aqueous dissolution of a template of solid water-soluble particles of calibrated size previously impregnated with organogel.

16. The method according to claim 15, wherein the microporous organogel is prepared from an organogelator comprising 12-hydroxystearic acid and an organic liquid non-miscible in water.

17. The method according to claim 16, wherein the organic liquid non-miscible in water comprises an oil that is soybean oil.

18. The method according to claim 15, wherein the template of solid water-soluble particles comprises one or more sugars or salts.

19. The method according to claim 15, wherein the template of solid water-soluble particles comprises one or more sucrose or sodium chloride.

* * * * *